United States Patent [19]

Irgang et al.

[11] Patent Number: 5,166,433
[45] Date of Patent: Nov. 24, 1992

[54] CATALYST AND THE AMINATION OF ALCOHOLS UNDER HYDROGENATING CONDITIONS

[75] Inventors: Matthias Irgang, Heidelberg; Juergen Schossig, Fussgoenheim; Wolfgang Schroeder, Bad Duerkheim; Siegfried Winderl, Heidelberg, all of Fed. Rep. of Germany

[73] Assignee: BASF Aktiengesellschaft, Ludwigshafen, Fed. Rep. of Germany

[21] Appl. No.: 638,391

[22] Filed: Jan. 7, 1991

Related U.S. Application Data

[62] Division of Ser. No. 457,334, Dec. 27, 1989, Pat. No. 5,002,922.

[30] Foreign Application Priority Data

Feb. 4, 1989 [DE] Fed. Rep. of Germany ....... 3903367

[51] Int. Cl.⁵ ................. C07C 209/26; C07C 209/16; C07D 295/023
[52] U.S. Cl. .................................... 564/106; 544/358; 544/404; 544/410; 564/472; 564/473; 564/474; 564/475; 564/479; 564/480
[58] Field of Search .............. 564/472, 479, 473, 474, 564/475, 480; 544/106, 358, 404, 410

[56] References Cited

U.S. PATENT DOCUMENTS

| | | | |
|---|---|---|---|
| 4,014,933 | 3/1977 | Boettger et al. | 564/447 |
| 4,153,581 | 5/1979 | Habermann | 502/331 |
| 4,524,102 | 1/1985 | Hostettler | 560/26 |
| 4,709,028 | 11/1987 | Johnson et al. | 544/106 |
| 4,736,030 | 4/1988 | Mueller et al. | 544/403 |
| 4,891,349 | 1/1990 | Bowman | 502/331 |
| 4,952,734 | 8/1990 | Weber et al. | 564/473 |

FOREIGN PATENT DOCUMENTS 0254335 1/1988 European Pat. Off.

Primary Examiner—Richard L. Raymond
Assistant Examiner—P. O'Sullivan
Attorney, Agent, or Firm—John H. Shurtleff

[57] ABSTRACT

Catalysts whose active material contains, in addition to from 20 to 85% by weight, calculated as $ZrO_2$, of oxygen-containing zirconium compounds, from 1 to 30% by weight, calculated as CuO, of oxygen-containing compounds of copper and from 1 to 40% by weight each, calculated as CoO or NiO, respectively, of oxygen-containing compounds of cobalt and of nickel are used for the amination of alcohols under hydrogenating conditions.

12 Claims, No Drawings

CATALYST AND THE AMINATION OF ALCOHOLS UNDER HYDROGENATING CONDITIONS

This application is a division, of application Ser. No. 457,334, filed Dec. 27, 1989, now U.S. Pat. No. 5,002,922.

The present invention relates to catalysts whose active material contains, in addition to from 20 to 85% by weight, calculated as $ZrO_2$, of oxygen-containing zirconium compounds, from 1 to 30% by weight, calculated as CuO, of oxygen-containing compounds of copper and from 1 to 40% by weight each, calculated as CoO or NiO, respectively, of oxygen-containing compounds of cobalt and of nickel.

The present invention furthermore relates to a process for the catalytic amination of alcohols under hydrogenating conditions with ammonia in the presence of hydrogen at elevated temperatures and under superatmospheric pressure.

DE-A-19 53 263 discloses that amines can be prepared by amination of the corresponding alcohols under hydrogenating conditions over supported catalysts containing cobalt, nickel and copper. The carrier used in these catalysts is alumina or silica. With these catalysts, it is possible to obtain good conversions provided that relatively high temperatures and pressures are used. If fairly low temperatures and pressures are employed, the conversion obtained with these catalysts decreases considerably, and the same applies to the selectivity of these catalysts in the preparation of certain amination products.

According to EP-A-254 335, Ni/Co/Ru catalysts on alumina or silica carriers which additionally contain halides in their active material are used for the amination of alcohols under hydrogenating conditions. However, with these catalysts too, conversions of not more than 61% are obtained at 200° C. and under 55 bar, the reaction product consisting of up to about 90% of primary amines. Dialkylamines can be obtained only in small amounts using this catalyst.

U.S. Pat. No. 4,151,204 describes catalysts for the specific preparation of amino alcohols. These catalysts, which consist of a metal, such as cobalt, nickel or copper, preferably nickel or copper, may additionally be doped with, inter alia, small amounts of zirconium, the zirconium being added in an atomic ratio of from 0.005 to 0.2 with respect to the nickel or cobalt. According to this patent, higher zirconium contents lead to side reactions, such as decomposition of the products.

It is an object of the present invention, since amines are intermediates of the chemical industry which are used in a variety of ways and required in large amounts, to improve the cost-efficiency- of conventional processes for the amination of alcohols under hydrogenating conditions. For this purpose, it was intended to provide catalysts which permit the amination of alcohols under hydrogenating conditions, even at relatively low temperatures and pressures, with high conversion and good yield and selectivity.

We have found that this object is achieved by catalysts whose active material contains, in addition to from 20 to 85% by weight, calculated as $ZrO_2$, of oxygen-containing zirconium compounds, from 1 to 30% by weight, calculated as CuO, of oxygen-containing compounds of copper and from 1 to 40% by weight each, calculated as CoO or NiO, respectively, of oxygen-containing compounds of cobalt and of nickel.

We have also found a process for the catalytic amination of alcohols under hydrogenating conditions with ammonia in the presence of hydrogen, at elevated temperatures and under superatmospheric pressure, wherein the catalyst used is one of the catalysts defined in the claims.

In general, the novel catalysts are preferably used in the form of solid catalysts. The term solid catalyst denotes a catalyst which, in contrast to a supported catalyst, consists only of catalytically active material. Solid catalysts can be used by introducing the catalytically active material, milled to a powder, into the reaction vessel, or milling the catalytically active material, mixing it with molding assistants, molding the mixture and heating it and then arranging the catalyst moldings, for example in the form of spheres, cylinders, rings or spirals, in the reactor.

The catalytically active material of the novel catalyst contains, in addition to oxygen-containing compounds of zirconium, oxygen-containing compounds of cobalt, of nickel and of copper.

Since the stated concentrations are based in each case on the catalytically active material of the catalyst, unless stated otherwise, the catalytically active material of the catalyst is defined below as the sum of the masses of the catalytically active components zirconium, cobalt, nickel and copper in the catalyst, calculated in each case as $ZrO_2$, CoO, NiO or CuO, after the final heat treatment of the catalyst or before its reduction with hydrogen. It is conventional in this art to calculate these active metals as their oxides even though the metals are initially provided as various oxygen-containing compounds.

In general, the zirconium oxide content of the novel catalysts is from 20 to 85, preferably from 70 to 80%, by weight.

The other components, cobalt, nickel and copper, are generally present altogether in amounts of from 15 to 80, preferably from 15 to 60, in particular from 15 to 50%, by weight in the catalytically active material.

Preferred catalysts contain in their catalytically active material from 20 to 85% by weight of oxygen-containing zirconium compounds, from 1 to 30% by weight of oxygen-containing copper compounds and from 1 to 40% by weight each of oxygen-containing compounds of cobalt and of nickel.

Particularly preferred catalysts prepared according to the invention are those whose active material contains, in addition to from 70 to 80% by weight of oxygen-containing zirconium compounds, from 1 to 10% by weight of oxygen-containing copper compounds and from 5 to 20% by weight each of oxygen-containing cobalt and nickel compounds.

There are various possible procedures for the preparation of the solid catalysts. They are obtainable, for example, by converting powder mixtures of hydroxides, carbonates, oxides and/or other salts of the components zirconium, cobalt, nickel and copper into a paste with water and then extruding and heating the material thus obtained.

In general, however, precipitation methods are used for the preparation of the novel catalysts. Thus, they can be obtained, for example, by coprecipitation of the cobalt, nickel and copper components from an aqueous salt solution containing these components, by means of a mineral base, in the presence of a suspension of a sparingly soluble, oxygen-containing zirconium compound, and subsequent washing, drying and calcination of the resulting precipitate. Examples of suitable sparingly soluble, oxygen-containing zirconium compounds are zirconium dioxide, zirconium oxide hydrate, zirconium phosphates, zirconium borates and zirconium silicates. The suspensions of the sparingly soluble zirconium compounds can be prepared by suspending fine-particled powders of these compounds in water with vigorous stirring; advantageously, these suspensions are obtained by precipitation of the sparingly soluble zirconium compounds from aqueous zirconium salt solutions by means of mineral bases.

The novel catalysts are preferably prepared by coprecipitation of all their components. For this purpose, an aqueous mineral base, in particular an alkali metal base, for example sodium carbonate, sodium hydroxide, potassium carbonate or potassium hydroxide, is added to an aqueous salt solution containing catalyst components at elevated temperatures and with stirring, until the precipitation is complete The type of salts used is in general not critical; since it is mainly the water solubility of the salts which is important in this procedure, their good water solubility, which is required for the preparation of these relatively highly concentrated salt solutions, is a criterion. Of course, in the selection of the salts of the individual components, the only salts chosen are those having anions which do not give rise to problems either by causing undesirable precipitation or by hindering or preventing precipitation owing to complex formation.

Novel catalysts having particularly advantageous properties are obtainable by precipitating some of the zirconium component of the catalyst, advantageously from an aqueous zirconium salt solution, separately in a precipitation apparatus by the addition of aqueous mineral bases. The remaining part of the zirconium component of the catalyst can then be coprecipitated together with the other catalytically active components, as described above, onto the resulting, preferably freshly precipitated zirconium oxide hydrate. As a rule, it is found particularly advantageous initially to precipitate from 10 to 80, preferably from 30 to 70, in particular from 40 to 60%, by weight of the total amount of zirconium of the catalytically active material.

The precipitates obtained in these precipitation reactions are generally chemically impure and consist of, inter alia, mixtures of the oxides, oxide hydrates, hydroxides, carbonates and insoluble and basic salts of the stated metals. It may prove advantageous with regard to the filterability of the precipitates if they are aged, i.e. if they are left to stand for some time after the precipitation, if necessary at elevated temperatures or under a stream of air.

The precipitates obtained after these precipitation processes are further processed in a conventional manner to the novel catalyts: after washing, they are generally dried at from 80° to 200° C., preferably from 100° to 150° C., and then calcined, in general at from 300° to 800° C., preferably from 400° to 600° C., in particular from 450° to 550° C.

After the calcination, the catalyst is advantageously conditioned, either by conversion to a certain particle size by milling, or by milling it and then mixing it with molding assistants, such as graphite or stearic acid, pressing on a tabletting press to give pellets and heating the latter The heating temperatures correspond in general to the temperatures during calcination.

The catalysts prepared in this manner contain the catalytically active metals in the form of a mixture of their oxygen-containing compounds, i.e. in particular as oxides and mixed oxides.

The catalysts prepared in this manner are stored and if necessary handled in this form. Before they are used as the catalysts for the amination of alcohols under hydrogenating conditions, they are usually reduced beforehand. However, they can also be used without prior reduction, in which case they are reduced under the conditions of amination with hydrogenation, by the hydrogen present in the reactor. For prior reduction, the catalysts are generally first exposed to a nitrogen/hydrogen atmosphere at from 150° to 200° C. for from 12 to 20 hours and then also treated in a hydrogen atmosphere for up to about 24 hours at from 200° to 300° C. During this prior reduction, some of the oxygen-containing metal compounds present in the catalyst is reduced to the corresponding metals, so that these are present, together with the various oxygen compounds, in the active form of the catalyst.

The catalysts prepared according to the invention are particularly suitable as catalysts for the amination of aliphatic alcohols under hydrogenating conditions. In this reaction, alcohols are converted into the corresponding amines in the presence of an aminating agent, for example ammonia, monoalkylamines or dialkylamines, and in the presence of hydrogen with the aid of a catalyst which acts as a hydrogenation/dehydrogenation catalyst. Regarding the mechanism of this reaction, it is assumed that the alcohol used is first dehydrogenated to the corresponding carbonyl compound and the latter then undergoes condensation with ammonia or with the amine to give the corresponding azomethine or enamine, which is then hydrogenated to the corresponding amine in the final step of the reaction sequence. Consequently, instead of the alcohols, the corresponding carbonyl compounds can also be equally successfully used in the amination under hydrogenating conditions. The use of carbonyl compounds in the said amination is thus equivalent to the use of the corresponding alcohols. Alcohols are generally preferably used for this reaction merely because they are readily available and economical.

Suitable starting materials are virtually all primary and secondary aliphatic alcohols. The aliphatic alcohols may be straight-chain, branched or cyclic. Like primary alcohols, secondary alcohols are also aminated. Regarding the number of carbon atoms of the alcohols which can be aminated, there are likewise no known restrictions to date. The alcohols may furthermore carry substituents which are inert under the conditions of amination with hydrogenation, for example alkoxy or alkyleneoxy groups. If it is intended to aminate polybasic alcohols, it is possible to obtain amino alcohols, cyclic amines or polyaminated products by controlling the reaction conditions.

For example, the following alcohols are preferably aminated: methanol, ethanol, propanol, isopropanol, butanol, pentanol, hexanol, 2-ethylhexanol, tridecanol, stearyl alcohol, palmityl alcohol, cyclohexanol, ethanolamine, propanolamine, isopropanolamine, hexanolamine, diethanolamine, N-alkyldiethanolamines, diisopropanolamine, ethylene glycol, propylene glycol, butanediol, pentanediol, hexanediol, 2,2-bis-(4-hydroxycyclohexyl)propane, propane, methoxyethanol, ethoxyethanol, propoxyethanol, butoxyethanol, polyethylene glycol ether, polypropylene glycol ether and polybutylene glycol ether. The last-mentioned polyalkylene glycol ethers are converted into the corresponding amines by transformation of their free hydroxyl groups in the novel reaction.

Suitable aminating agents in the amination of alcohols under hydrogenating conditions are both ammonia and primary or secondary, aliphatic or cycloaliphatic amines.

When ammonia is used as the aminating agent, the alcohol hydroxyl groups are first converted into the free amino groups ($-NH_2$). The primary amines thus formed can react with further alcohol to form the corresponding secondary amines, and these in turn can react with further alcohol to give the corresponding, symmetric tertiary amines. Depending on the composition of the reaction mixture and on the reaction conditions used (pressure, temperature and reaction time), primary, secondary or tertiary amines can be preferably prepared in this manner, depending on requirements.

Cyclic amines, such as pyrrolidines, piperidines, piperazines and morpholines, can be prepared in this manner from polybasic alcohols by intramolecular amination under hydrogenating conditions.

Besides ammonia, it is possible to use primary or secondary amines as aminating agents. These aminating agents are preferably used for the preparation of asymmetrically substituted di- or trialkylamines, such as ethyldiisopropylamine and ethyldicyclohexylamine. For example, the following mono- and dialkylamines are preferably used as aminating agents: methylamine, dimethylamine, ethylamine, diethylamine, propylamine, diisopropylamine, butylamine, pentylamine, hexylamine and cyclohexylamine.

The aminating agent can be used in a stoichiometric amount, based on the alcoholic hydroxyl group to be aminated However, an excess of the aminating agent is preferably used, in general more than a 5 molar excess per mole of alcoholic hydroxyl groups to be aminated. Ammonia in particular is generally used in an excess of from 5 to 250, preferably from 10 to 100, in particular from 25 to 80, moles per mole of alcoholic hydroxyl groups to be reacted. Greater excess amounts of both ammonia and primary or secondary amines are possible.

The hydrogen is generally fed to the reaction in an amount of from 5 to 400, preferably from 50 to 200, 1 (S.T.P.) per mole of alcohol component.

The reaction is generally carried out without an additional solvent In the reaction of high molecular weight or highly viscous starting compounds or products or of those which are solid at room temperature, it may be advantageous concomitantly- to use a solvent which is inert under the reaction conditions, such as tetrahydrofuran, dioxane, N-methylpyrrolidone or ethylene glycol dimethyl ether.

The reaction is usually carried out at above 100° C., in particular above 170° C., preferably from 180° to 230° C. In general, the reaction is carried out under a pressure of more than 10 bar, preferably from 30 to 400, in particular from 30 to 300, bar.

The use of higher temperatures and of a higher total pressure is possible. The total pressure in the reaction vessel, which is the sum of the partial pressure of the aminating agent, of the alcohol component and of the reaction products formed and of any concomitantly used solvent at the stated temperatures, is advantageously adjusted to the desired reaction pressure by forcing in hydrogen.

It may be advantageous for the selectivity of the present process if the catalyst moldings in the reactor are mixed, i.e. diluted, with inert packing The amount of packing in such catalyst formulations may be from 20 to 80, in particular from 30 to 60, very particularly from 40 to 50, parts by volume.

In practice, the reaction is generally carried out as follows: the alcohol and the aminating agent are fed simultaneously to the catalyst, which is usually present in a fixed-bed reactor, preferably heated from outside, at the desired reaction temperature and the desired pressure. The space velocity over the catalyst is in general from 0.02 to 0.5, preferably from 0.05 to 0.3, particularly preferably from 0.08 to 0.15, 1 of alcohol per 1 of catalyst per hour. It is advantageous to heat the reactants before feeding them to the reaction vessel, the reactants preferably being heated to the reaction temperature.

The reactor may be operated by the liquid phase or trickle-bed method, i.e. the reactants can be passed through the reactor either from bottom to top or from top to bottom. Of course, the process can be carried out either batchwise or continuously. In both cases, the excess aminating agent can be circulated together with the hydrogen. If the conversion in the reaction is complete, the unconverted starting material may likewise be recycled to the reaction zone.

The reacted mixture is advantageously let down, after which the excess aminating agent and the hydrogen are removed from it and the resulting aminated products are purified by distillation, liquid extraction or crystallization. The excess aminating agent and the hydrogen are advantageously recycled to the reaction zone. The same applies to any unconverted or incompletely converted alcohol components.

The water of reaction formed in the course of the reaction generally does not have an adverse effect on the degree of conversion, the reaction rate, the selectivity and the catalyst life and is therefore advantageously not removed from the reaction product until the latter is being worked up by distillation.

The amines obtainable in this manner are used, inter alia, as intermediates in the preparation of surfactants, drugs, crop protection agents and vulcanization accelerators.

The Examples which follow illustrate the invention. The superiority of the novel catalysts compared with the conventional supported catalysts used for the amination of alcohols under hydrogenating conditions and based on alumina carriers, according to DE-A-19 53 263, is evident in particular in Examples 1 and 2. Compared with the conventional catalysts, it is possible with the novel catalysts to obtain substantially higher conversions under significantly lower pressures and, in the case of Examples 1 and 2, substantially higher selectivities in the preparation of morpholine. The comparison of the novel solid catalyst A with the zirconium dioxide supported catalyst B prepared by the impregnation process, which otherwise have the same elemental composition, clearly illustrates that, in the novel catalysts, it is not simply that the alumina carrier has been exchanged for a zirconium dioxide carrier but that the oxygen-containing zirconium compounds are a component of the catalytically active material and these zirconium compounds in this form are important for the advantageous properties of the catalyst.

EXAMPLES

Examples 1 and 2 below were carried out using a solid catalyst prepared according to the invention (catalyst A) and a novel supported catalyst (catalyst B) and, for comparison, a catalyst according to DE-A-19 53 263 (catalyst C).

In all Examples, the yields stated are based on the converted starting material.

PREPARATION OF THE CATALYSTS

Catalyst A

A solution of a zirconium salt, copper(II) salt, cobalt-(II) salt and nickel(II) salt was pumped simultaneously with sodium carbonate solution having a density of 1.208 kg/l into a precipitation apparatus containing freshly precipitated zirconium oxide suspended in water. The pH of the solution was kept constant at 6.0 during the precipitation, and was increased to 7.5 after the metal salt solution had been consumed. The precipitate was washed, dried to constant weight at 120° C. and calcined to constant weight at 400° C. The resulting crude catalyst material was milled, mixed with 3% by weight of graphite, pelletized and calcined again at 520° C. for 3 hours. Composition:

76% by weight of Zr, calculated as $ZrO_2$,
4% by weight of Cu, calculated as CuO,
10% by weight of Co, calculated as CoO, and
10% by weight of Ni, calculated as NiO.

Catalyst B

A pure zirconium dioxide carrier prepared by extrusion was impregnated with a solution containing cobalt nitrate, copper nitrate and nickel nitrate but no zirconium compound and was then dried at 120° C. This procedure was repeated several times. After the final calcination at 520° C., the composition was as follows:

76% by weight of Zr, calculated as $ZrO_2$,
4% by weight of Cu, calculated as CuO,
10% by weight of Co, calculated as CoO, and
10% by weight of Ni, calculated as NiO.

Catalyst C

A catalyst mentioned in DE-B-19 53 263 was prepared by a procedure similar to that for the preparation of catalyst B, by repeated impregnation of an extruded alumina carrier with the cobalt nitrate, copper nitrate and nickel nitrate solution used for the preparation of catalyst B. After calcination at 520° C., the catalyst had the following composition:

76% by weight of Al, calculated as $Al_2O_3$,
4% by weight of Cu, calculated as CuO,
10% by weight of Co, calculated as CoO, and
10% by weight of Ni, calculated as NiO.

EXAMPLE 1

Amination of diethylene glycol under hydrogenating conditions

A reactor containing 500 cm³ of the corresponding, pre-reduced catalyst was charged with 90 cm³ of diethylene glycol and 350 cm³ of liquid ammonia per hour. The catalyst temperature was brought to 200° C., and the pressure in the reactor was adjusted to 30 bar by simultaneously forcing in hydrogen. The reacted mixture was let down, after which excess ammonia was distilled off from this mixture. Analysis of the reacted mixtures obtained using catalysts A, B and C gave the data shown in Table 1.

TABLE 1

|  | Catalyst A | Catalyst B | Catalyst C |
|---|---|---|---|
| Conversion of diethylene glycol [%] | 89.5 | 71.1 | 49.7 |
| Yield of |  |  |  |
| a) aminoethoxyethanol [%] | 10.0 | 22.7 | 65.9 |
| b) morpholine [%] | 82.5 | 58.3 | 28.2 |

EXAMPLE 2

Amination of diethylene glycol under hydrogenating conditions

The reaction was carried out similarly to Example 1, except that the pressure in the reaction vessel was brought to 200 bar. The results listed in Table 2 were obtained using catalysts A, B and C.

TABLE 2

|  | Catalyst A | Catalyst B | Catalyst C |
|---|---|---|---|
| Conversion of diethylene glycol [%] | 99.7 | 85.8 | 81.5 |
| Yield of |  |  |  |
| a) aminoethoxyethanol [%] | 0.5 | 15.6 | 21.9 |
| b) morpholine [%] | 92.8 | 62.9 | 66.7 |

EXAMPLE 3

Amination of n-butanol under hydrogenating conditions

A procedure similar to that described in Example 1 was used and 90 cm³/hour of n-butanol were reacted with 300 cm³/hour of liquid ammonia at 180° C. and under 30 bar over catalyst A.

Conversion of n-butanol: 92%.
Yield:
a) 51% of n-butylamine
b) 43% of di-n-butylamine
c) 5% of tri-n-butylamine.

EXAMPLE 4

Amination of tridecanol under hydrogenating conditions

The experiment of Example 3 was repeated, the alcohol reacted being n-tridecanol instead of n-butanol.

Conversion of tridecanol: 99%.
Yield:
a) 19% of n-tridecylamine
b) 72% of di-n-tridecylamine
c) 8% of tri-n-tridecylamine.

EXAMPLE 5

Amination of ethanolamine under hydrogenating conditions

A procedure similar to that described in Example 1 was used and 30 cm³/hour of ethanolamine were reacted with 300 cm³/hour of liquid ammonia at 220° C. and under 30 bar over catalyst A.

Conversion of ethanolamine: 100%.
Yield of piperazine: 92%.

EXAMPLE 6

Amination of 2-dimethylaminoethan-1-ol under hydrogenating conditions

In a reactor, 100 cm$^3$ of 2-dimethylaminoethan-1-ol and 2000 cm$^3$ of liquid ammonia were passed per hour over 1000 cm$^3$ of previously reduced catalyst A. During the reaction, the temperature was maintained at 120° C. and the pressure was kept at 250 bar by forcing in hydrogen. Excess ammonia was distilled off from the reacted mixture.

Conversion of 2-dimethylaminoethan-1-ol: 90%.
Yield: 2-dimethylaminoethyl-1-amine: 84%

EXAMPLE 7

Amination of N-ethyldiethanolamine under hydrogenating conditions 0.1 l of N-ethyldiethanolamine per l of catalyst per hour and 5 l of liquid ammonia per hour were passed, by the trickle-bed procedure, at 200° C., through a fixed-bed reactor which had been charged with 5 l of a catalyst bed consisting of 60 parts by volume of catalyst A and 40 parts by volume of packing. The pressure in the reactor was brought to 250 bar by forcing in hydrogen. After the end of the reaction, the pressure was let down to 20 bar and excess ammonia was distilled off. Thereafter, the pressure was let down to atmospheric pressure and the reaction mixture was subjected to fractional distillation. In the distillation, 99% pure N-ethylpiperazine was obtained The conversion was complete.
Yield: 79%.

EXAMPLE 8

Amination of N-butyldiethanolamine under hydrogenating conditions

N-Butylpiperazine was prepared from N-butyldiethanolamine similarly to Example 7 and was obtained in 99.5% purity. The conversion was complete.
Yield: 75%.

We claim:

1. In the process for the catalytic amination of an alcohol or carbonyl compound to obtain the corresponding amine under hydrogenating conditions with an aminating agent in the presence of hydrogen at elevated temperatures and under superatmospheric pressure, the improvement which comprises:

using for said amination a catalyst whose active material contains, in addition to from 20 to 85% by weight, calculated as $ZrO_2$, of an oxygen-containing zirconium compound, from 1 to 30% by weight, calculated as CuO, of an oxygen-containing compound of copper and from 1 to 40% by weight each, calculated as CoO and NiO, respectively, of an oxygen-containing compound of cobalt and of nickel.

2. A process as claimed in claim 1, wherein the active material of said catalyst contains, in addition to from 70 to 80% by weight, calculated as $ZrO_2$, of an oxygen-containing zirconium compound, from 1 to 10% by weight, calculated as CuO of an oxygen-containing compound of copper and from 5 to 20% by weight each, calculated as CuO and NiO, respectively, of an oxygen-containing compound of cobalt and of nickel.

3. A process as claimed in claim 1, wherein the active material of said catalyst is obtained by coprecipitation of the water-soluble compounds of the stated elements by means of a mineral base and subsequent washing, drying and calcining of the resulting precipitate.

4. A process as claimed in claim 1, wherein the active material of said catalyst is obtained by the following measures:
   a) precipitation of some of the zirconium component form an aqueous zirconium salt solution by means of a mineral base,
   b) coprecipitation of the remaining part of the zirconium component with the remaining catalyst components form an aqueous solution of these components by means of a mineral base in the presence of the zirconium oxide hydrate precipitated beforehand in stage a), and
   c) washing, drying and calcining the precipitate.

5. A process as claimed in claim 1, wherein the active material is obtained by coprecipitation of water-soluble compounds of cobalt, of nickel and of copper by means of a mineral base in the presence of an initially taken, sparingly soluble oxygen-containing zirconium compound, and subsequently washing, drying and calcining the resulting precipitate.

6. A process as claimed in claim 1, wherein the compound subjected to the catalytic amination is a primary or secondary aliphatic alcohol.

7. A process as claimed in claim 1, wherein the compound subjected to the catalytic amination is the carbonyl compound obtained by dehydrogenation of a primary or secondary aliphatic alcohol.

8. A process as claimed in claim 1, wherein the alcohol used as starting material for catalytic amination under hydrogenating conditions is selected from the group consisting of methanol, ethanol, propanol, isopropanol, butanol, pentanol, hexanol, 2-ethylhexanol, tridecariol, stearyl alcohol, palmityl alcohol, cyclohexanol, ethanolamine, propanolamine, isopropanolamine, hexanolamine, diethanolamine, N-alkyldiethanolamines, diisopropanolamine, ethylene glycol, propylene glycol, butanediol, pentanediol, hexandediol, 2,2-bis-(4-hydroxycyclohexyl)-propane, methoxyethanol, ethoxyethanol, propoxyethanol, butyoxethanol, polyethylene glycol ether, polypropylene glycol ether, and polybutylene gycol ether.

9. A process as claimed in claim 1, wherein diethylene gycol is aminated under hydrogenating conditions to obtain morpholine as the product.

10. A process as claimed in claim 1, wherein ethanolamine is aminated under hydrogenating conditions to obtain piperazine.

11. A process as claimed in claim 1, wherein N-ethyldiethanolamine is aminated under hydrogenating conditions to obtain N-ethylpiperazine.

12. A process as claimed n claim 1, wherein N-butyldiethanalamine is aminated under hydrogenating conditions to obtain N-butylpiperazine.

* * * * *

UNITED STATES PATENT AND TRADEMARK OFFICE
CERTIFICATE OF CORRECTION

PATENT NO. : 5,166,433
DATED : November 24, 1992
INVENTOR(S) : Irgang et al.

It is certified that error appears in the above-identified patent and that said Letters Patent is hereby corrected as shown below:

Column 9:

Claim 1, line 1, first occurrence: change "the" to --a--.

Column 10:

Claim 4, line 5 and line 9, each occurrence: change "form" to --from--.

Claim 8, line 12: change "butyoxethanol" to --butoxyethanol--.

Claim 12, lines 1 and 2: change "N-butyldiethanalamine" to --N-butyldiethanolamine--.

Signed and Sealed this

Nineteenth Day of October, 1993

Attest:

BRUCE LEHMAN

*Attesting Officer*     *Commissioner of Patents and Trademarks*